United States Patent [19]

Schreiber

[11] 4,327,209

[45] Apr. 27, 1982

[54] PROCESS FOR THE PRODUCTION OF DIBENZAZOLYL COMPOUNDS

[75] Inventor: Werner Schreiber, Basel, Switzerland

[73] Assignee: Ciba-Geigy Corporation, Ardsley, N.Y.

[21] Appl. No.: 211,481

[22] Filed: Nov. 28, 1980

[30] Foreign Application Priority Data

Dec. 6, 1979 [CH] Switzerland ............... 10829/79

[51] Int. Cl.$^3$ ............. C07D 413/06; C07D 405/04; C07D 409/14

[52] U.S. Cl. ...................... 542/466; 542/467; 548/217; 548/219; 548/220; 548/327; 548/328

[58] Field of Search ............ 542/466, 467; 548/217, 548/219, 220, 327, 328

[56] References Cited

U.S. PATENT DOCUMENTS

| | | | |
|---|---|---|---|
| 3,135,762 | 6/1964 | Maeder et al. | 548/220 |
| 3,575,996 | 4/1971 | Liechti et al. | 548/219 |
| 4,110,246 | 8/1978 | Frischkorn et al. | 548/220 |

FOREIGN PATENT DOCUMENTS

| | | |
|---|---|---|
| 1469207 | 9/1970 | Fed. Rep. of Germany . |
| 2306050 | 8/1973 | Fed. Rep. of Germany . |
| 2349803 | 4/1975 | Fed. Rep. of Germany . |
| 2436279 | 2/1976 | Fed. Rep. of Germany . |
| 2645301 | 4/1977 | Fed. Rep. of Germany . |
| 2715567 | 10/1978 | Fed. Rep. of Germany . |
| 2750947 | 5/1979 | Fed. Rep. of Germany . |
| 2809117 | 9/1979 | Fed. Rep. of Germany . |
| 94996 | 1/1973 | German Democratic Rep. . |
| 97209 | 4/1973 | German Democratic Rep. . |

*Primary Examiner*—Arthur P. Demers
*Attorney, Agent, or Firm*—Edward McC. Roberts

[57] ABSTRACT

Benzazolyl compounds of the formula

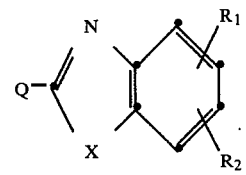

wherein $R_1$ and $R_2$ are specific substituents, X is oxygen or $R_3N-$, Q is a radical of the formula

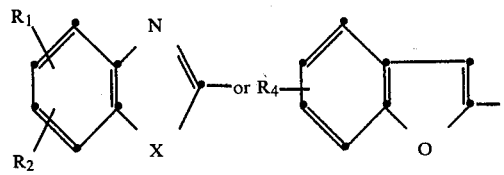

wherein $R_4$ denotes specific substituents, and A is 2,5-furylene, 2,5-thenylene or a bridge member which contains at least one double bond between 2 carbon atoms or is the direct bond. These compounds are obtained by condensation of organic carboxylic acids with aminobenzenes in diphenyl ether or a mixture of diphenyl ether and diphenyl.

11 Claims, No Drawings

PROCESS FOR THE PRODUCTION OF DIBENZAZOLYL COMPOUNDS

The present invention relates to a process for the production of dibenzazolyl compounds.

Processes for the production of dibenzazolyl compounds by condensation of organic dicarboxylic acids with aminobenzenes in the presence of organic solvents and of catalysts are known from the literature. For example, the production of α,β-di-[aryloxazol-(2)-yl)]-ethylenes from 1-amino-2-hydroxybenzene and tartaric acid or malic acid, in higher boiling hydrocarbons of the benzene series or chlorinated benzene derivatives such as xylene or chlorobenzene, are known from U.S. Pat. Nos. 2,842,545 and 2,995,605 and from British Pat. No. 835 894. The production of 2,5-di-[benzimidazol-(2')-yl]-furanes by condensation of furane-2,5-dicarboxylic acid with a 1,2-diaminobenzene in the presence of boric acid and in the absence of a solvent, is described in U.S. Pat. No. 3,103,518, wherein reference is made to the fact that the presence of a high boiling solvent results in less good yields. Similar 2,5-di-[benzimidazol-(2')-yl]-furanes are obtained according to British Pat. No. 950 890 by carrying out the condensation of furane-2,5-dicarboxylic acid with 1,2-diaminobenzene in the presence of a high boiling aliphatic free or etherified hydroxyl compound, especially glycerol, as solvent, and boric acid as condensation agent. The production of bis-(benzoxazolyl)thiophenes from o-hydroxyamino-benzenes and dicarboxylic acids in the presence of a catalyst such as zinc chloride or boric acid, and optionally in a higher boiling polar solvent, is described in U.S. Pat. No. 3,135,762. All these processes, however, have the drawback that the final products are obtained in unsatisfactory yields.

The present invention has for its object to provide a process which makes it possible to obtain dibenzazolyl compounds in better yields and in shorter reaction times.

Surprisingly, it has been found that dibenzazolyl compounds can be obtained in good yield and in shorter reaction times by carrying out the condensation of the organic dicarboxylic acid with the aminobenzene in a specific mixture of solvents.

The process of the present invention for the production of benzazolyl compounds of the formula

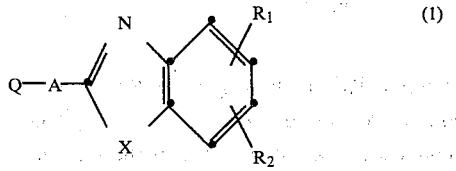

by condensation, in the presence of a solvent and a catalyst, and at elevated temperature, of organic carboxylic acids of the formula

and

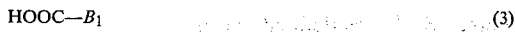

wherein B is the 5-carboxy-fur-(2)-yl radical, the HOOC—CHOH—CH$_2$— or HOOC—CHOH—CHOH— radical or a benzoxazol-(2)-yl radical, and B$_1$ is the 5-carboxy-then-(2)-yl radical, HOOC—CHOH—CH$_2$— or HOOC—CHOH—CHOH— radical, with aminobenzenes of the formulae

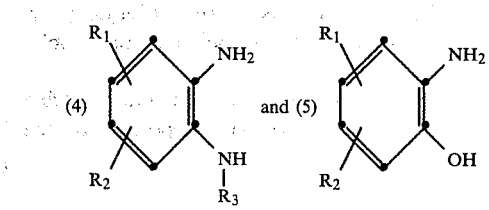

wherein R$_1$ is hydrogen, halogen, lower alkyl, lower alkoxy, hydroxy-lower alkyl, —COCN or —COO— lower alkyl, R$_2$ is hydrogen, halogen, lower alkyl, lower alkoxy, hydroxy-lower alkyl, —COCN or —COO— lower alkyl, X is oxygen or a R$_3$N-group, wherein R$_3$ is hydrogen, lower alkyl, hydroxy-lower alkyl, phenyl or benzyl, A is 2,5-furylene, 2,5-thenylene, a bridge member containing at least one double bond between 2 carbon atoms, or is the direct bond, and Q is a radical of the formula

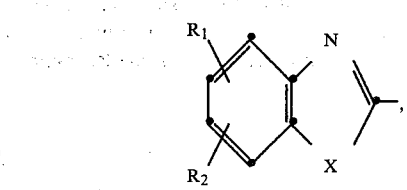

wherein X, R$_1$ and R$_2$ are as defined above, and, if A is the direct bond, Q is also a radical of the formula

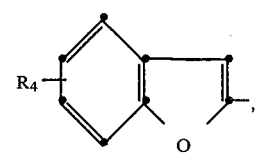

wherein R$_4$ is hydrogen, lower alkyl, lower alkoxy or halogen, comprises the use of diphenyl ether, or a mixture of diphenyl ether and diphenyl, as solvent.

As solvent it is preferred to use a eutectic mixture of 73.5% by volume of diphenyl ether and 26.5% by volume of diphenyl.

The term "lower" used to qualify substituents throughout this specification denotes that these substituents contain 1 to 4 carbon atoms.

Examples of suitable carboxylic acids for the process of the invention are furane-2,5-dicarboxylic acid, thiophene-2,5-dicarboxylic acid, tartaric acid, malic acid, and benzofurane-2-carboxylic acid.

Examples of suitable aminobenzenes for the process of the invention are o-diaminobenzenes, one amino group of which is primary and the other is at least secondary, as well as o-aminophenols such as 4-methyl-1,2-diaminobenzene, 4-methoxy-1,2-diaminobenzene, 4,5-dimethyl-1,2-diaminobenzene, 4-isopropyl-1,2-diaminobenzene, 1-amino-2-(methylamino)benzene, o-phenylenediamine, 1-amino-2-(β-hydroxyethylamino)-benzene, 1-amino-2-(ethylamino)benzene, 1-amino-2-(benzylamino)benzene, 4-chloro-1,2-diaminobenzene, 4-tert-butyl-1,2-diaminobenzene, 2-aminophenol, 2-amino-4-methylphenol, 2-amino-5-methylphenol, 2- amino-4,6-dimethylphenol, 2-amino-4-tert-butylphenol, 2-amino-4-methoxyphenol, 2-amino-4-chlorophenol and 2-amino-4,6-dichlorophenol.

Examples of suitable catalysts are zinc chloride, polyphosphoric acid, p-toluenesulfonic acid and, preferably, boric acid.

The process of the present invention is most suitable for the production of benzazolyl compounds of the formula

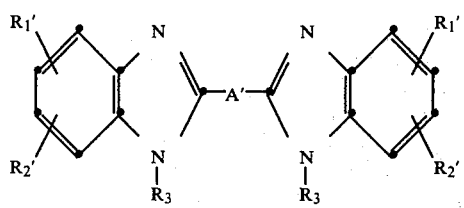
(6)

wherein $R_1'$ is hydrogen, lower alkyl or hydroxy-lower alkyl, $R_2'$ is hydrogen, lower alkyl or hydroxy-lower alkyl, $R_3$ is hydrogen, lower alkyl, hydroxy-lower alkyl, phenyl or benzyl, and $A'$ is the 2,5-furylene radical or the vinylene radical, by condensation of a dicarboxylic acid of the formula

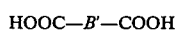
HOOC—B'—COOH (7)

wherein B' is the 2,5-furylene radical or the —CH₂—CHOH— radical, with an aminobenzene of the formula

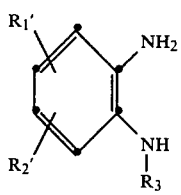

wherein $R_1'$, $R_2'$ and $R_3$ are as defined above, as well as for the production of benzazolyl compounds of the formula

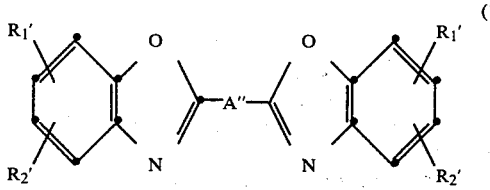
(13)

wherein $R_1'$ is hydrogen, lower alkyl or hydroxy-lower alkyl, $R_2'$ is hydrogen, lower alkyl or hydroxy-lower alkyl, and A" is the 2,5-thenylene radical or the vinylene radical, by condensation of a dicarboxylic acid of the formula

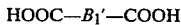
HOOC—B₁'—COOH (14)

wherein $B_1'$ is the 2,5-thenylene radical or the —CH₂—CHOH— radical, with an aminobenzene of the formula

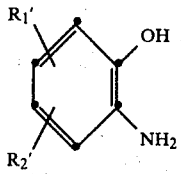
(15)

wherein $R_1'$ and $R_2'$ are as defined above.

The process of the invention is of especial interest for the production of benzazolyl compounds of the formula

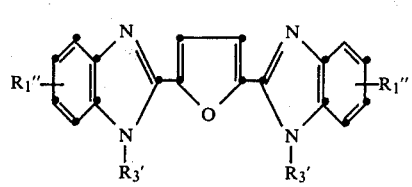
(9)

wherein $R_1''$ is hydrogen, methyl or β-hydroxyethyl, and $R_3'$ is hydrogen, methyl or benzyl, by condensation of 2,5-furanedicarboxylic acid with an aminobenzene of the formula

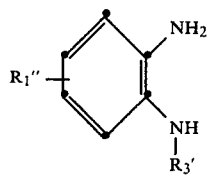
(10)

wherein $R_1''$ and $R_3'$ are as defined above, and of the formula

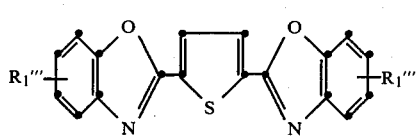
(16)

wherein $R_1'''$ is hydrogen, lower alkyl or COO-lower alkyl, by condensation of 2,5-thiophenedicarboxylic acid with an aminobenzene of the formula

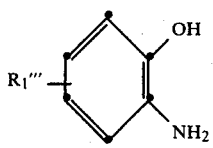
(17)

wherein $R_1'''$ is as defined above.

The process of the invention is especially preferred for the production of benzazolyl compounds of the following formulae:

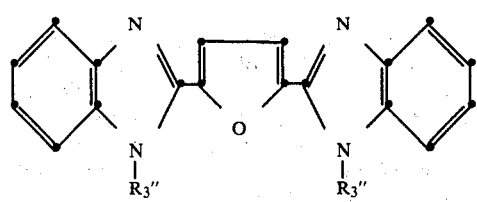

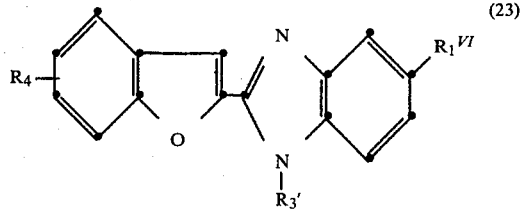

wherein $R_3''$ is hydrogen or methyl, by condensation of 2,5-furanedicarboxylic acid with an aminobenzene of the formula

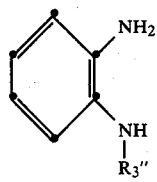

wherein $R_3''$ has the above meaning;

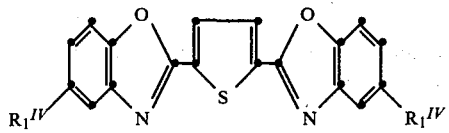

wherein $R_1^{IV}$ is hydrogen or tert-butyl, by condensation of 2,5-thiophenedicarboxylic acid with an aminobenzene of the formula

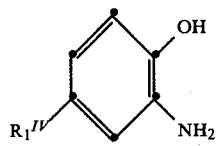

wherein $R_1^{IV}$ has the above meaning;

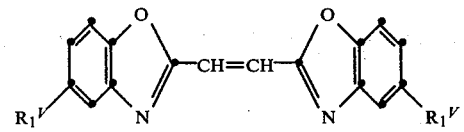

wherein $R_1^V$ is hydrogen or methyl, by condensation of malic acid of the formula $$HOOC-CH_2-CHOCH-COOH \quad (21)$$

with an aminobenzene of the formula

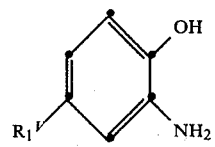

wherein $R_1^V$ has the above meaning;

wherein $R_1^{VI}$ is hydrogen or lower alkyl, $R_3'$ is hydrogen, methyl or benzyl, and $R_4$ is hydrogen, lower alkyl, lower alkoxy or halogen, by condensation of a carboxylic acid of the formula

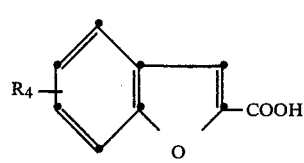

wherein $R_4$ has the above meaning, with an aminobenzene of the formula

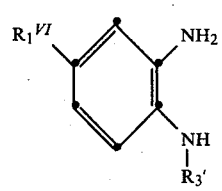

wherein $R_1^{VI}$ and $R_3'$ have the above meanings; and

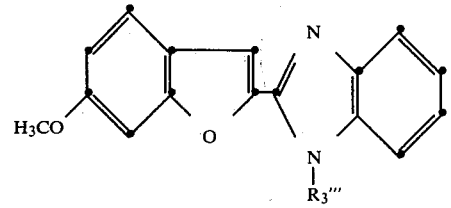

wherein $R_3'''$ is methyl or benzyl, by condensation of 6-methoxy-benzofurane-2-carboxylic acid with an aminobenzene of the formula

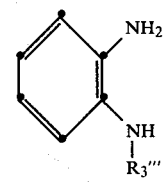

wherein $R_3'''$ has the above meaning.

The process of the invention is suitable not only for the production of symmetrical, but also of asymmetrical, benzazolyl compounds, which compounds can be obtained by condensation of the organic carboxylic acids of the formulae (2) and (3) with two different aminobenzenes of the formulae (4) and (5). The carboxylic acid is reacted with the aminobenzene in the molecular ratio 1:2 to produce symmetrical benzazolyl compounds, in the molecular ratio 1:1:1 to produce asymmetrical compounds, and in the molecular ratio 1:1 to produce the benzofuranebenzazoles e.g of the formula (23).

The condensation of the organic carboxylic acids of the formulae (2) and (3) with the aminobenzenes of the formulae (4) and (5) is carried out in the temperature range from 130° to 250° C., with exclusion of air or in a nitrogen atmosphere and under reduced atmospheric pressure, e.g. 25 to 800 mbar. For the condensation, the carboxylic acids can be used as such or in the form of suitable functional derivatives, e.g. in the form of acid halides.

The benzazole compounds obtained by the process of the present invention are known fluorescent whitening agents for different organic materials.

The following Examples illustrate the invention, but imply no restriction to what is described therein. Percentages are by weight, unless otherwise states.

EXAMPLE 1

A reaction vessel is charged with 255.1 g of 2-amino-4-tert-butylphenol (100%), 8.7 g of boric acid, 129.1 g of thiophene-2,5-dicarboxylic acid (100%), and 455 ml of a eutectic mixture of 73.5% by volume of diphenyl ether and 26.5% by volume of diphenyl. The apparatus is evacuated and the vacuum is displaced with nitrogen. With stirring, the reaction mixture is heated to 190°–235° C. while distilling off water. As soon as 30 ml of water are distilled off, the apparatus is evacuated to 800 mbar and condensation is continued for a further 45 minutes under these pressure conditions. The vacuum is then increased to 400 mbar and the reaction mixture is kept for 4 hours at 230°–235° C. The reaction mixture is concentrated in vacuo by distilling off 300 ml of the eutectic mixture of diphenyl/diphenyl ether and cools simultaneously to 140°–150° C. The vacuum is then displaced with nitrogen and, as soon as the product has crystallised out, 560 ml of methanol are slowly introduced. The reaction mixture is refluxed for 30 minutes, cooled, and the crystallised precipitate is filtered with suction, washed with 500 ml of methanol and then with 300 ml of deionised water, and dried in a vacuum cabinet at 100° C., affording 315 g (97% of theory) of the compound of the formula

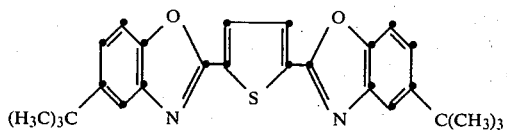

which, after recrystallisation from the eutectic mixture, has a melting point of 199°–200° C.

EXAMPLE 2

The procedure of Example 1 is repeated, using 168.6 g of 2-aminophenol (100%) instead of 255.2 g of 2-amino-4-tert-butylphenol. Yield: 232 g (97% of theory) of the compound of the formula

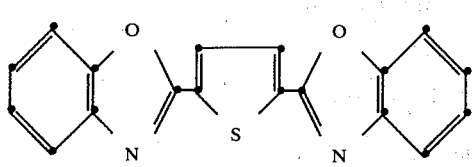

with a melting point of 216°–217° C.

EXAMPLE 3

A reaction vessel is charged with 123.1 g of 2-amino-4-methylphenol, 67.7 g of malic acid, 367.5 g of diphenyl ether and 132.5 g of diphenyl. The reaction vessel is evacuated to 90 mbar and the reaction mixture is heated to 135° C. and kept for 3 hours at this temperature. The vacuum is displaced with nitrogen and 3 g of boric acid are added. The reaction vessel is again evacuated and the mixture is heated to 155° C. The batch is condensed at this temperature and under a pressure of 50 mbar for 13 hours. The reaction mixture is then concentrated and cooled. To the crystallised product are added 500 ml of methanol and the mixture is refluxed for 30 minutes, then cooled to 20° C. and stirred at this temperature for 1 hour. The precipitate is filtered with suction, washed with four 100 ml portions of methanol and then with 400 ml of deionised water, affording 127 g (86% of theory) of the compound of the formula

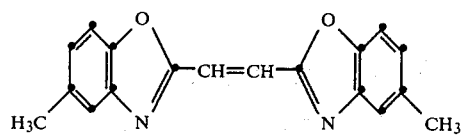

which, after recrystallisation from xylene, has a melting point of 183°–184° C.

EXAMPLE 4

The procedure of Example 1 is repeated, using 117 g of furane-2,5-dicarboxylic acid instead of thiophene-2,5-dicarboxylic acid, and 166.5 g of phenylenediamine or 188.5 g of N-methylphenylenediamine instead of 2-amino-tert-butylphenol. The product obtained is the compound of the formula

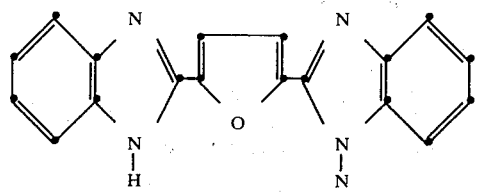

with a melting point of 310° C., or, respectively, the compound of the formula

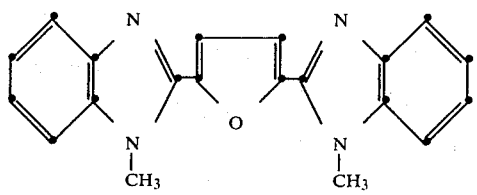

with a melting point of 272° C.

EXAMPLE 5

A reaction vessel is charged with 96.1 g of 6-methoxy-benzofurane-2-carboxylic acid, 99.2 g of N-benzyl-o-phenylenediamine, 5 g of boric acid, and 400 ml of a eutectic mixture of diphenyl/diphenyl ether. The suspension is heated in an atmosphere of nitrogen and under a pressure of 50 to 150 mbar to 170°–180° C., and kept for 6 hours in this temperature range. The reaction solution is then concentrated, whereupon the product crystallises out, affording 147 g of the compound of the formula

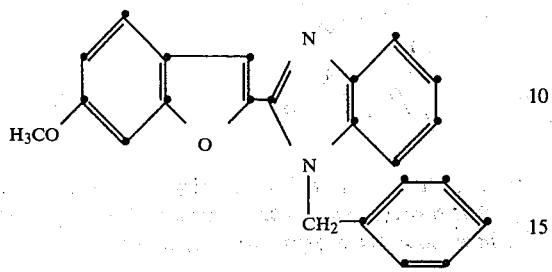

with a melting point of 142° C.

What is claimed is:
1. A process for the production of benzazolyl compounds of the formula

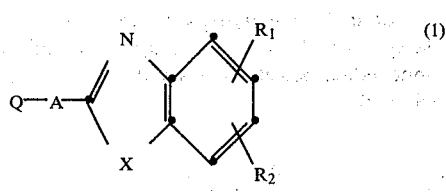 (1)

by condensation, in the presence of a solvent and a catalyst, of organic carboxylic acids of the formulae

HOOC—B and

HOOC—$B_1$ wherein B is the 5-carboxy-fur-(2)-yl radical, the HOOC—CHOH—CH$_2$— or HOOC—CHOH—CHOH— radical or a benzoxazol-(2)-yl radical, and $B_1$ is the 5-carboxy-then-(2)-yl radical, HOOC—CHOH—CH$_2$— or HOOC—CHOH—CHOH— radical, with aminobenzenes of the formulae

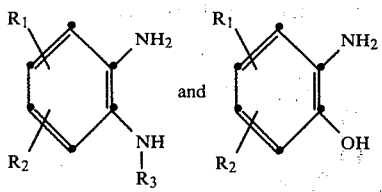

wherein $R_1$ is hydrogen, halogen, lower alkyl, lower alkoxy, hydroxy-lower alkyl, —COCN or —COO— lower alkyl, $R_2$ is hydrogen, halogen, lower alkyl, lower alkoxy, hydroxy-lower alkyl, —COCN or —COO— lower alkyl, X is oxygen or a $R_3$N-group, wherein $R_3$ is hydrogen, lower alkyl, hydroxy-lower alkyl, phenyl or benzyl, A is 2,5-furylene, 2,5-thenylene, a bridge member containing at least one double bond between 2 carbon atoms, or is the direct bond, and Q is a radical of the formula

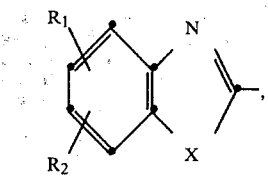

wherein X, $R_1$ and $R_2$ are as defined above, and, if A is the direct bond, Q is also a radical of the formula

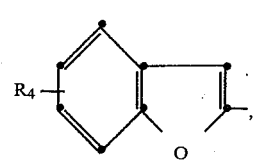

wherein $R_4$ is hydrogen, lower alkyl, lower alkoxy or halogen, which process comprises carrying out said condensation in a eutectic mixture of 73.5% by volume of diphenyl ether and 26.5% by volume of diphenyl as solvent.

2. A process according to claim 1, wherein the condensation is carried out under reduced pressure.

3. A process according to claim 2 for the production of benzazolyl compounds of the formula

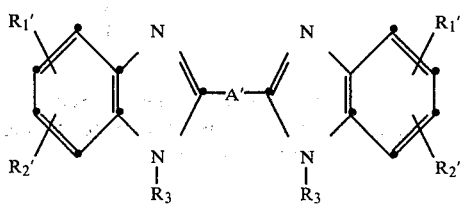

wherein $R_1'$ is hydrogen, lower alkyl or hydroxy-lower alkyl, $R_2'$ is hydrogen, lower alkyl or hydroxy-lower alkyl, $R_3$ is hydrogen, lower alkyl, hydroxy-lower alkyl, phenyl or benzyl, and A' is the 2,5-furylene radical or the vinylene radical, which process comprises condensing a dicarboxylic acid of the formula

HOOC—B'—COOH wherein B' is the 2,5-furylene radical or the —CH$_2$—CHOH— radical, with an aminobenzene of the formula

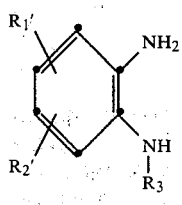

wherein $R_1'$, $R_2'$ and $R_3$ are as defined above.

4. A process according to claim 3 for the production of benzazolyl compounds of the formula

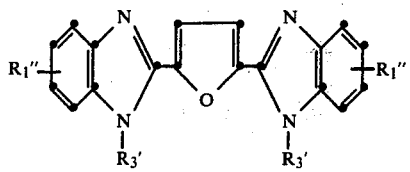

wherein $R_1''$ is hydrogen, methyl or $\beta$-hydroxyethyl, and $R_3'$ is hydrogen, methyl or benzyl, which process comprises condensing 2,5-furanedicarboxylic acid with an aminobenzene of the formula

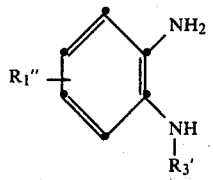

wherein $R_1''$ and $R_3'$ are as defined above.

5. A process according to claim 4 for the production of benzazolyl compounds of the formula

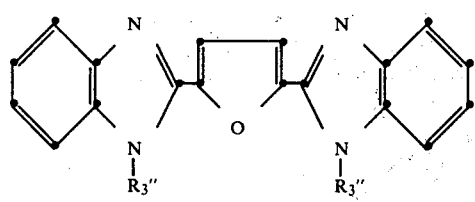

wherein $R_3''$ is hydrogen or methyl, which process comprises condensing 2,5-furanedicarboxylic acid with an aminobenzene of the formula

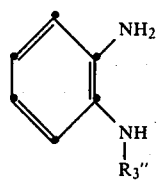

wherein $R_3''$ is as defined above.

6. A process according to claim 2 for the production of benzazolyl compounds of the formula

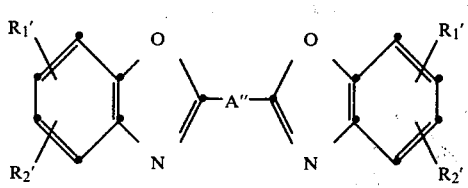

wherein $R_1'$ is hydrogen, lower alkyl or hydroxy-lower alkyl, $R_2'$ is hydrogen, lower alkyl or hydroxy-lower alkyl, and $A''$ is the 2,5-thenylene radical or the vinylene radical, which process comprises condensing a dicarboxylic acid of the formula $$HOOC{-}B_1'{-}COOH$$

wherein $B_1'$ is the 2,5-thenylene radical or the $-CH_2-CHOH-$ radical, with an aminobenzene of the formula

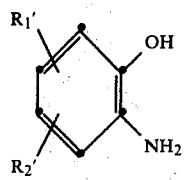

wherein $R_1'$ and $R_2'$ are as defined above.

7. A process according to claim 2 for the production of benzazolyl compounds of the formula

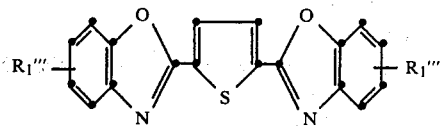

wherein $R_1'''$ is hydrogen, lower alkyl or COO-lower alkyl, which process comprises condensing 2,5-thiophenedicarboxylic acid with an aminobenzene of the formula

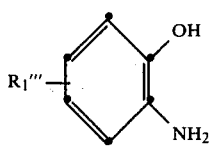

wherein $R_1'''$ is as defined above.

8. A process according to claim 7 for the production of benzazolyl compounds of the formula

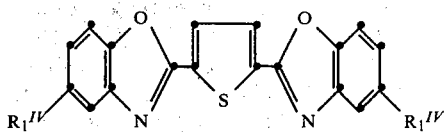

wherein $R_1^{IV}$ is hydrogen or tert-butyl, which process comprises condensing 2,5-thiophenedicarboxylic acid with an aminobenzene of the formula

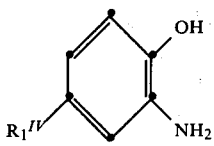

wherein $R_1^{IV}$ is as defined above.

9. A process according to claim 6 for the production of benzazolyl compounds of the formula

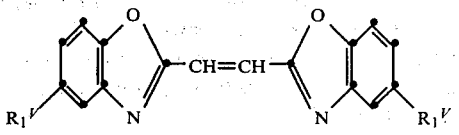

wherein $R_1^V$ is hydrogen or methyl, which process comprises condensing malic acid of the formula

HOOC—CH$_2$—CHOCH—COOH with an aminobenzene of the formula

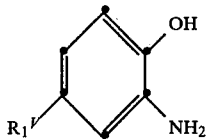

wherein $R_1^V$ is as defined above.

10. A process according to claim 1 for the production of benzazolyl compounds of the formula

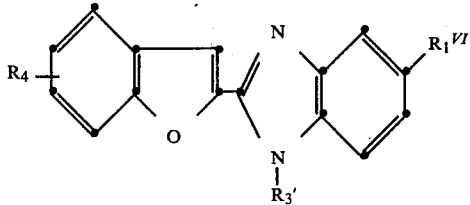

wherein $R_1^{VI}$ is hydrogen or lower alkyl, $R_3'$ is hydrogen, methyl or benzyl, and $R_4$ is hydrogen, lower alkyl, lower alkoxy or halogen, which process comprises condensing a carboxylic acid of the formula

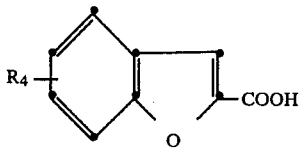

wherein $R_4$ is as defined above, with an aminobenzene of the formula

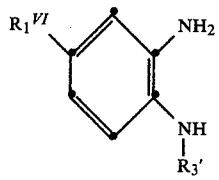

wherein $R_1^{VI}$ and $R_3'$ are as defined above.

11. A process according to claim 10 for the production of benzazolyl compounds of the formula

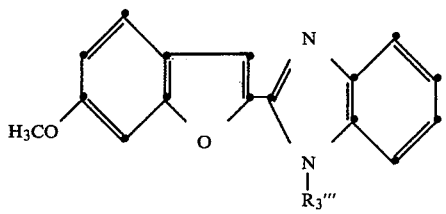

wherein $R_3'''$ is methyl or benzyl, which process comprises condensing 6-methoxybenzofurane-2-carboxylic acid with an aminobenzene of the formula

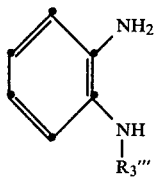

wherein $R_3'''$ is as defined above.

* * * * *